(12) United States Patent
Duffin et al.

(10) Patent No.: US 10,004,886 B2
(45) Date of Patent: Jun. 26, 2018

(54) DUAL APPLICATOR

(71) Applicant: NoDK, LLC, Lake Oswego, OR (US)

(72) Inventors: Marcus Duffin, Tigard, OR (US); Steve Duffin, Wilsonville, OR (US)

(73) Assignee: ORAL HEALTH OUTREACH, LLC, Keizer, OR (US)

( * ) Notice: Subject to any disclaimer, the term of this patent is extended or adjusted under 35 U.S.C. 154(b) by 392 days.

(21) Appl. No.: 14/745,186

(22) Filed: Jun. 19, 2015

(65) Prior Publication Data

US 2015/0374965 A1    Dec. 31, 2015

Related U.S. Application Data

(60) Provisional application No. 62/018,387, filed on Jun. 27, 2014.

(51) Int. Cl.
| | |
|---|---|
| *A61M 35/00* | (2006.01) |
| *A61M 5/31* | (2006.01) |
| *A61C 19/06* | (2006.01) |
| *A61J 1/06* | (2006.01) |

(52) U.S. Cl.
CPC ......... *A61M 35/003* (2013.01); *A61C 19/063* (2013.01); *A61M 5/3134* (2013.01); *A61J 1/067* (2013.01)

(58) Field of Classification Search
CPC .............. A61M 35/003; A61M 35/006; A61M 5/3134; A61C 19/063
See application file for complete search history.

(56) References Cited

U.S. PATENT DOCUMENTS

| | | | |
|---|---|---|---|
| 3,467,096 A | 9/1969 | Horn | |
| 5,454,786 A | 10/1995 | Harris | |
| 6,783,514 B2 | 8/2004 | Tovey et al. | |
| 8,262,608 B2 | 9/2012 | Clark et al. | |
| 2003/0060746 A1* | 3/2003 | Mark | A45D 34/042 604/3 |
| 2008/0195040 A1* | 8/2008 | Clark | A61B 17/00491 604/87 |
| 2011/0092918 A1* | 4/2011 | Jensen | A61M 35/003 604/264 |

OTHER PUBLICATIONS

International Search Report and Written Opinion dated Oct. 1, 2015 for International Application No. PCT/US2015/036785, 13 pages.
Chu, C. H. et al., "Arresting rampant dental caries with silver diamine fluoride in a young teenager suffering from chronic oral graft versus host disease post-bone marrow transplantation: a case report", BMC Research Notes, Jan. 2014, vol. 7, pp. 1-14.

* cited by examiner

*Primary Examiner* — Ariana Zimbouski
(74) *Attorney, Agent, or Firm* — Schwabe, Williamson & Wyatt, P.C.

(57) ABSTRACT

Embodiments herein may relate to a unit dose system that may include a first applicator and a second applicator. The first applicator may include a crushable ampoule that includes approximately 1 milliliter (mL) of a silver salt solution disposed therein. The first applicator may further include a first syringe tip coupled with the crushable ampoule. The second applicator may include a flexible filled tube that includes approximately 4 mL of a varnish disposed therein and a second syringe tip coupled with the flexible filled tube. Other embodiments may be described and/or claimed.

6 Claims, 3 Drawing Sheets

DUAL APPLICATOR

CROSS-REFERENCE TO RELATED APPLICATIONS

This application claims priority to U.S. Provisional Application 62/018,387 filed Jun. 27, 2014 and titled "APPARATUS FOR SOLUTION TRANSPORT AND APPLICATION," the entire disclosure of which is incorporated herein in its entirety.

TECHNICAL FIELD

The present disclosure relates to an apparatus, system, or method for packaging and transport of solutions such as topical dental solutions.

BACKGROUND

The background description provided herein is for the purpose of generally presenting the context of the disclosure. Unless otherwise indicated herein, the materials described in this section are not prior art to the claims in this application and are not admitted to be prior art by inclusion in this section.

There are many different kinds of topical solutions that may serve a medical, dental, or aesthetic purpose. These different topical solutions may vary quite significantly in the amount of solution used for a given application and the packaging composition the solution may be held in. Some solutions may only be available for sale in volumes that are much higher than is needed for each application, allowing for application to multiple individuals. Some solutions may also be light sensitive and/or reactive with plastics. Packaging of some solutions may also not allow for easy or convenient topical application of that solution under different sets of circumstances or sites of application.

Based on these above described variables there may be loss of efficacy of the solution due to reactivity with plastic packaging, or improper topical application of the solution when applied in a different location than the packaging originally intended.

BRIEF DESCRIPTION OF THE DRAWINGS

Embodiments are illustrated by way of example and not by way of limitation in the figures of the accompanying drawings, in which like references indicate similar elements and in which.

DETAILED DESCRIPTION

Various aspects of the illustrative embodiments will be described using terms commonly employed by those skilled in the art to convey the substance of their work to others skilled in the art. However, it will be apparent to those skilled in the art that alternate embodiments may be practiced with only some of the described aspects. For purposes of explanation, specific devices and configurations are set forth in order to provide a thorough understanding of the illustrative embodiments. However, it will be apparent to one skilled in the art that alternate embodiments may be practiced without the specific details. In other instances, well-known features are omitted or simplified in order not to obscure the illustrative embodiments.

Further, various operations will be described as multiple discrete operations, in turn, in a manner that is most helpful in understanding the present disclosure. However, the order of description should not be construed as to imply that these operations are necessarily order dependent. In particular, these operations need not be performed in the order of presentation.

The phrase "in one embodiment" is used repeatedly. The phrase generally does not refer to the same embodiment; however, it may. The terms "comprising," "having," and "including" are synonymous, unless the context dictates otherwise.

In providing some clarifying context to language that may be used in connection with various embodiments, the phrases "A/B" and "A and/or B" mean (A), (B), or (A and B); and the phrase "A, B, and/or C" means (A), (B), (C), (A and B), (A and C), (B and C) or (A, B and C).

The term "coupled with," along with its derivatives, may be used herein. "Coupled" may mean one or more of the following. "Coupled" may mean that two or more elements are in direct physical contact. However, "coupled" may also mean that two or more elements indirectly contact each other, but yet still cooperate or interact with each other, and may mean that one or more other elements are coupled or connected between the elements that are said to be coupled with each other.

Figure 1:
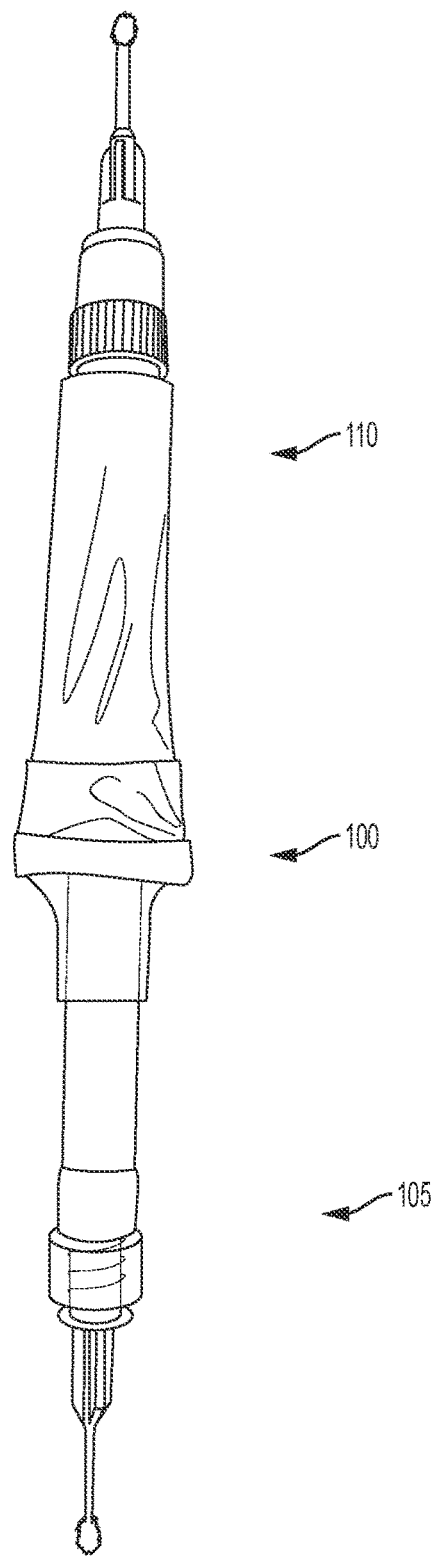
FIG. 1 is an example of a dual applicator system, in accordance with various embodiments.

FIG. 1 depicts an example of a unit dose system 100. The unit dose system may include a first applicator 105 and a second applicator 110. In embodiments, the unit dose system 100 may allow for the direct topical application of two different solutions that have different packaging requirements. For example, the first applicator 105 and the second applicator 110 may include different solutions, as described in detail below. Generally, the unit dose system 100 may be used in dental applicators to topically apply the solutions of the different applicators in a convenient manner. In embodiments, the solutions of the first applicator 105 may include dissolved silver salts such as silver nitrate (AgN), silver diamine fluoride ($Ag(NH_3)_2F$), silver chloride (AgCl), and/or silver carbonate ($Ag_2CO_3$). The solution of the second applicator 110 may include a solution such as an approximately 5% sodium fluoride varnish, an approximately 1-10% chlorhexidine varnish, copal varnish, glass ionomer cement, sealant, cavity liner or bonding agents. In other embodiments, the respective solutions of the first applicator 105 or second applicator 110 may be solutions used in industries such as podiatry, dermatology, botany, veterinary, or some other industry where topical application of the solutions may be desirable. In embodiments, the solution of the first applicator may have different packaging requirements than the solution of the second applicator. For example, one or both of the solutions may be light sensitive, reactive with plastic, and/or more stable in smaller volumes.

Figure 2:
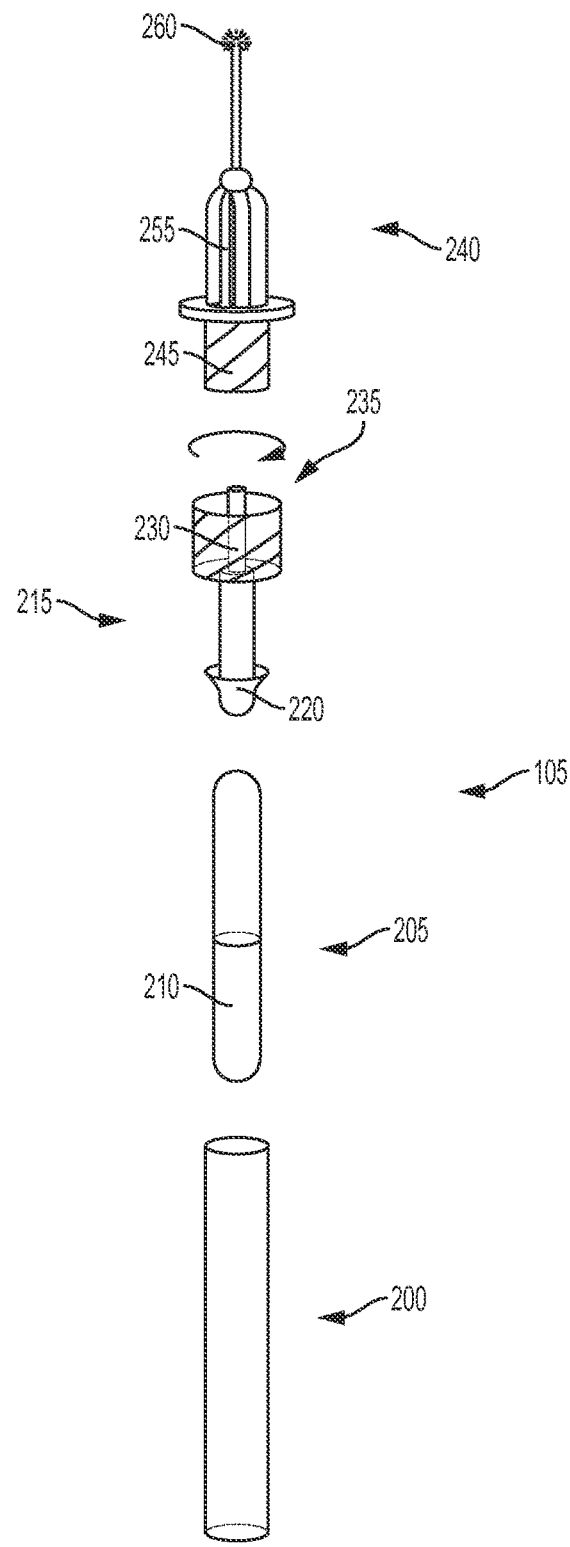
FIG. 2 is an exploded view of one applicator of the dual applicator system of FIG. 1, in accordance with various embodiments.

FIG. 2 depicts an exploded view of the first applicator 105 of FIG. 1. The first applicator 105 may include a hollow tube at 200. The hollow tube 200 may have a crushable ampoule 205 positioned therein. The crushable ampoule 205 may include a first solution 210 that may be, for example dissolved silver salts such as silver nitrate (AgN), silver diamine fluoride ($Ag(NH_3)_2F$), silver chloride (AgCl), and/ or silver carbonate ($Ag_2CO_3$). Specifically, in some embodiments, the solution 210 may be a 50% silver nitrate solution which may include a silver nitrate salt dissolved in a non-reactive carrier water at a ratio of approximately 50 grams (g) of silver nitrate salt per approximately 100 milliliters (ml) of water. In embodiments, the crushable ampoule 205 may hold approximately up to approximately 1 ml of the solution 210.

The hollow tube 200 may be sealed at a first end, and coupled with a syringe tip adaptor 215 at a second end. The syringe tip adaptor 215 may include a barb 220 that is inserted into the second end of the hollow tube 200. The barb 220 may be relatively flexible, and generally have a diameter that is larger than the diameter of the hollow tube 200. That way, when the barb 220 is inserted into the hollow tube 200, the barb 220 may be compressed and push against the sides of the hollow tube, thereby forming a seal that may be air tight and/or water tight. Although FIG. 2 may depict only a single barb 220, in other embodiments the syringe tip adaptor 215 may have two or more barbs configured to be inserted into the hollow tube 200 to form the air tight and/or water tight seal.

Generally, the barb 220 may be on a first end of the syringe tip adaptor 215, and the second end of the syringe tip adaptor 215 may include a female leur lock 235. In some embodiments, the syringe tip adaptor 215 may include one or more ridges 230 that may help a user to grip the syringe tip adaptor 215.

The second end of the syringe tip adaptor 215, that is the female leur lock 235, may couple with a syringe tip 240. The syringe tip 240 may include a male leur thread 245 that is configured to couple with the female leur thread 235 to form an air and/or water tight seal. The syringe tip 240 may further include one or more external ridges 255 by which a user may be able to grip the syringe tip 240 securely. The syringe tip 240 may further include a brush tip 260.

Generally, the hollow tube 200 may be relatively flexible, and the glass ampoule 205 may be relatively brittle. As a result, a user may be able to apply pressure to the hollow tube to break the crushable ampoule 205, thereby releasing the solution 210 into the hollow tube. Continued squeezing of the hollow tube 200 (and/or gravity) may cause the solution 210 to flow through the syringe tip adaptor 215, and exit the syringe tip 240 via the brush tip 260. In some embodiments where it is desired to topically apply the solution 210 to a surface, a user may brush the solution 210 onto the surface using the brush tip 260.

In embodiments, the hollow tube 200 may be plastic, or some other material. The crushable ampoule 205 may be glass. In embodiments, the material that the hollow tube 200 and/or the glass ampoule 205 are formed of may be dependent on the chemical makeup of the solution 210.

Although the syringe tip adaptor 215 is depicted as a leur-to-barb type adaptor, in other embodiments the syringe tip adaptor 215 could be some other type of adaptor such as an integral lock ring leur, a leur-to-thread adaptor, a coupler, a panel mount, a tapered seal adaptor, etc. The integral lock ring leur, leur-to-barb, or tapered seal adaptors may create an air/water tight seal with the hollow tube 200. In some embodiments, a leur-to-thread adaptor, coupler, or panel mount may create an air and/or water tight seal with the hollow tube 200 if the hollow tube 200 had screw-type threads that may effectively mate with the adaptor.

Generally, the crushable ampoule 205 containing the solution 210 may prevent the solution 210 from touching or otherwise coming into contact with the hollow tube 200 if the solution 210 was reactive to the material of the hollow tube 200. For example, if the hollow tube 200 is plastic, and the solution 210 is reactive with plastic, the storage of the solution 210 in the crushable ampoule 205 may prevent the solution 210 from coming into contact with the plastic of the hollow tube 200 for an extended period of time such as during storage and/or transport. This prevention of contact could be desirable if, for example, the solution 210 was reactive with the plastic of the hollow tube 200 in such a manner that the effectiveness of the solution 210 would be reduced or otherwise affected by extended contact with the plastic. In some embodiments, the hollow tube 200 may contain UV inhibitors or opaque coloring in the plastic to reduce or eliminate light entering the hollow tube 200. This inhibition of light may be useful if, for example, the solution 210 was photoreactive. In other embodiments, the first applicator 105 may include an outer sleeve (not shown) that prevents light from interacting with the solution 210 to protect the solution 210 if it is sensitive to light.

Figure 3:
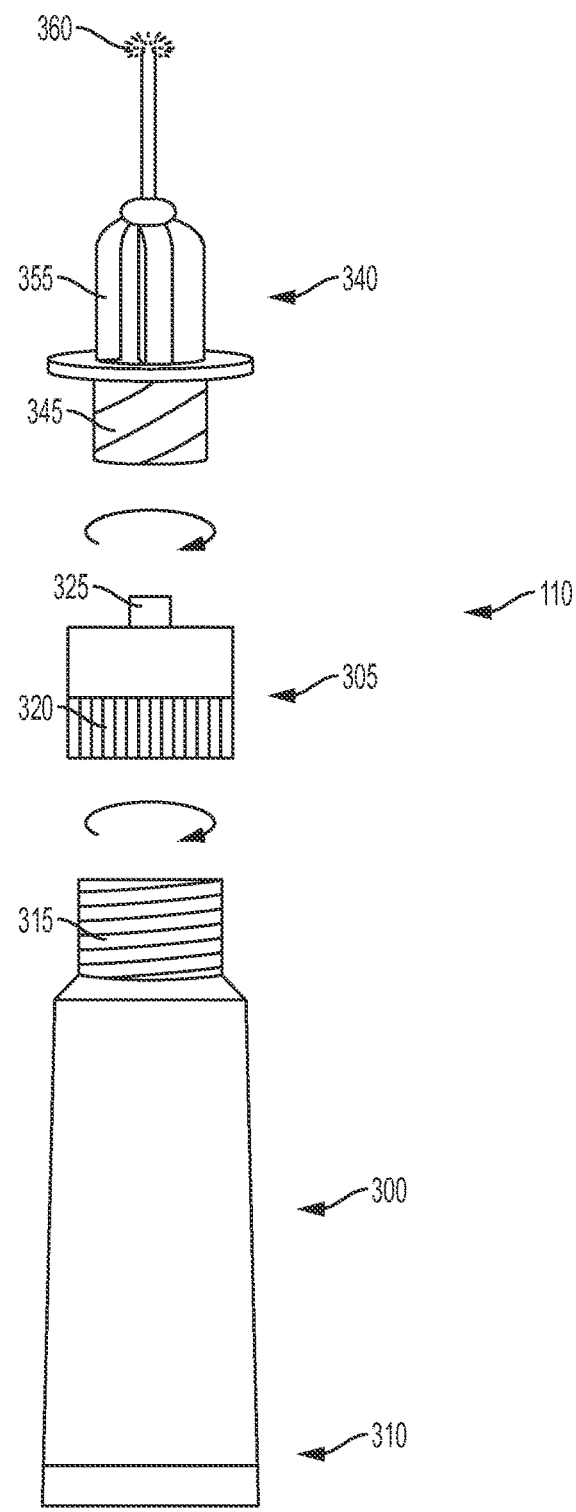
FIG. 3 is an exploded view of one applicator of the dual applicator system of FIG. 1, in accordance with various embodiments.

FIG. 3 depicts an exploded view of the second applicator 110 of FIG. 1. The second applicator may include a filled tube 300. The second applicator may further include a syringe tip adaptor 305 and a syringe tip 340. Generally, the syringe tip 340 may be similar to the syringe tip 240 of FIG. 2. Specifically, the syringe tip 340 may include a male leur lock 345, ridges 355, and a brush tip 360 that may be respectively similar to male leur lock 245, external ridges 255, and brush tip 260.

The filled tube 300 may contain a solution such as an approximately 5% sodium fluoride varnish, an approximately 1-10% chlorhexidine varnish, copal varnish, glass ionomer cement, sealant, cavity liner or bonding agents, as described above. Specifically, the filled tube may have approximately 4 ml of the solution. The filled tube 300 may have a sealed end 310 at a first end of the filled tube 300. The filled tube 300 may further include male threads 315 at a second end of the filled tube 300 opposite the first end.

The syringe tip adaptor 305 may include female threads 320 at a first end of the syringe tip adaptor 305, and a female leur lock 325 at a second end of the syringe tip adaptor 305 opposite the first end. The female threads 320 may be configured to mate with the male threads 315 to create a water and/or air tight seal between the filled tube 300 and the syringe tip adaptor. The female leur lock 325 may be configured to mate with the male leur lock 345 as described above with female leur lock 325 and male leur lock 345.

As described above, the syringe tip adaptor 305 is described herein as a thread-to-leur type adaptor. In other embodiments, the syringe tip adaptor 305 could be a different type of adaptor such as an integral lock ring leur, a coupler, a leur-to-barb type adaptor, a coupler, a panel mount, a tapered seal adaptor, etc.

In operation, the user may apply pressure to the filled tube 300, which may cause the solution to flow through the syringe tip adaptor 305, and exit the syringe tip 340 via the brush tip 360. In some embodiments where it is desired to topically apply the solution 310 to a surface, a user may brush the solution 310 onto the surface using the brush tip 360.

In some embodiments, the second end of filled tube 300 opposite the sealed end 310 may include an air/water tight seal. In order to allow the solution to exit the filled tube 300, a user may puncture the seal prior to applying pressure to the filled tube 300. In some embodiments, the user may unscrew the syringe tip 340 and insert the brush tip into the second end of the filled tube 300 to puncture the seal. In some embodiments, the user may insert the syringe tip 340 through the opening in the female leur thread 325 of the syringe tip adaptor 305, while in other embodiments the user may first remove the syringe tip adaptor. After puncturing the seal in the filled tube, the user may then re-connect the filled tube 300, syringe tip adaptor 305, and syringe tip 340 and use the second applicator 110 as described above.

In some embodiments, the filled tube 300 may be opaque. In other embodiments, the filled tube 300 may be transparent and/or semi-transparent. In some embodiments, the filled tube 300 may include UV inhibitors, as described above. In some embodiments, the filled tube 300 may be formed of a relatively non-reactive metal such as aluminum, while in other embodiments the filled tube 300 may be formed of plastic and/or some other type of material.

Returning to FIG. 1, it may be seen that the first applicator 105 and the second applicator 110 may be coupled to one another either permanently or removeably. Specifically, the sealed end 310 of the filled tube 300 may be coupled with the sealed end of the hollow tube 200, as shown in FIG. 1. When coupled to one another, the unit dose system 100 may measure between approximately 7 inches and 8 inches in length, as measured from brush tip 260 to brush tip 360. Because the unit dose system 100 is relatively small and easily held in a user's hand, the user may be able to easily and effectively transport the unit dose system 100 without damaging the solutions of the first or second applicators 105/110. Additionally, it may be possible for a user to easily and conveniently apply both the solution of applicator 105 and applicator 110 using only one hand, thereby quickly and efficiently topically applying the solutions in a place where complicated systems, transport, or storage mechanisms may be unavailable or undesirable.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A unit dose system comprising:
    a first applicator that includes:
        a glass ampoule with a silver salt solution that includes approximately 50 percent of a silver nitrate solution disposed therein;
        a plastic tube that surrounds the glass ampoule, wherein the plastic tube has a first end and a second end that is sealed;
        a first syringe tip adaptor coupled with the first end of the plastic tube, wherein the first syringe tip adaptor includes a barb that is inserted into the first end of the plastic tube, and wherein the barb has a diameter that is larger than a diameter of the plastic tube, and wherein the first syringe tip adaptor includes a first female luer lock on a side of the first syringe tip adaptor opposite the barb; and
        a first syringe tip that includes a first male luer lock coupled with the first female luer lock on a first side of the first syringe tip, and a first brush tip on a second side of the first syringe tip; and
    a second applicator coupled with the first applicator, wherein the second applicator includes:
        a flexible filled tube with a varnish disposed therein, wherein the varnish includes approximately 5 percent of a sodium fluoride solution, and wherein the flexible filled tube includes a first end that is sealed and a second end that is coupled with a second syringe tip adaptor on a first side of the second syringe tip adaptor, wherein the second syringe tip adaptor further includes a second female luer lock on a second side of the second syringe tip adaptor opposite the first side of the second syringe tip adaptor; and
        a second syringe tip that includes a second male luer lock coupled with the second female luer lock on a first side of the second syringe tip adaptor, and a second brush tip on a second side of the second syringe tip adaptor opposite the first side.

2. The unit dose system of claim 1, wherein the unit dose system has a length between the first brush tip and the second brush tip of 7 inches.

3. The unit dose system of claim 1, wherein the second end of the plastic tube is directly coupled with the first end of the flexible filled tube.

4. The unit dose system of claim 1, wherein the glass ampoule is crushable.

5. The unit dose system of claim 1, wherein pressure to the flexible filled tube causes the varnish to exit from the flexible filled tube, through the second syringe tip adaptor, and exit the second applicator via the second brush tip.

6. The unit dose system of claim 1, wherein a water tight seal is formed when the barb is inserted into the plastic tube.

* * * * *